(12) United States Patent
Omote et al.

(10) Patent No.: US 7,130,373 B2
(45) Date of Patent: Oct. 31, 2006

(54) METHOD AND APPARATUS FOR FILM THICKNESS MEASUREMENT

(75) Inventors: Kazuhiko Omote, Akiruno (JP); Akihiro Himeda, Ome (JP)

(73) Assignee: Rigaku Corporation, Tokyo (JP)

( * ) Notice: Subject to any disclaimer, the term of this patent is extended or adjusted under 35 U.S.C. 154(b) by 96 days.

(21) Appl. No.: 11/042,879

(22) Filed: Jan. 25, 2005

(65) Prior Publication Data

US 2005/0220267 A1    Oct. 6, 2005

(30) Foreign Application Priority Data

Jan. 28, 2004  (JP) .............................. 2004-019783

(51) Int. Cl.
*G01N 23/20* (2006.01)
(52) U.S. Cl. .......................................... 378/71; 378/70
(58) Field of Classification Search ................. 378/50, 378/54, 70, 71, 86, 89, 90; 250/559.27
See application file for complete search history.

(56) References Cited

U.S. PATENT DOCUMENTS 6,873,681 B1 *  3/2005  Toraya et al. .................. 378/71

FOREIGN PATENT DOCUMENTS

| JP | 04-194611 | 7/1992 |
| JP | 10-038821 | 2/1998 |
| JP | 10-103942 | 4/1998 |
| JP | 2000-088776 A | 3/2000 |

OTHER PUBLICATIONS

H. Toraya et al: "Quantitative basis for the rocking-curve measurement of preferred orientation in polycrystalline thin films", Journal of Applied Crystallography, ISSN 0021-8898, Feb. 7, 2003, International Union of Chrystallography, Great Britain, 2003; pp. 890-897.

* cited by examiner

*Primary Examiner*—Edward J. Glick
*Assistant Examiner*—Jurie Yun
(74) *Attorney, Agent, or Firm*—Frishauf, Holtz, Goodman & Chick, P.C.

(57) ABSTRACT

The thickness of a thin film can be measured based on the X-ray diffraction method. An X-ray is allowed to be incident upon a surface of the thin film. An intensity of a diffracted X-ray is measured with the incident angle $\alpha$ being changed to obtain a measured rocking curve. On the other hand, a theoretical rocking curve is calculated in consideration of an orientation density distribution function $\rho$ of the thin film. A scale factor is predetermined for a standard sample having a known film thickness. A parameter fitting operation is carried out in a manner that the characteristic parameter of the function $\rho$ and the film thickness t are adjusted so that the theoretical rocking curve including the scale factor can approach the measured rocking curve as closely as possible.

7 Claims, 16 Drawing Sheets

FIG. 8

Normalizing condition $$\int_0^{\pi/2} d\phi \sin\phi \int_0^{2\pi} d\xi \, \rho(\phi, \xi, z) = 1 \quad \cdots (1)$$

Gaussian function $$\rho(\phi, \xi, z) = G(H(z)) \exp\left[-(4 \ln 2)\left[\frac{\phi}{H(z)}\right]^2\right] \quad \cdots (2)$$

$$G = \left\{ 2\pi \int_0^{\pi/2} d\phi \sin\phi \exp\left[-(4 \ln 2)\left[\frac{\phi}{H(z)}\right]^2\right] \right\}^{-1} \quad \cdots (3)$$

FIG. 10

$$Q = \frac{N_0^2 \lambda^3}{\sin 2\theta_0} |F(hkl)|^2 \left(\frac{e^2}{mc^2}\right)^2 \frac{1+\cos^2 2\theta_0}{2} \quad \cdots (4)$$

$$\frac{L \Delta \alpha}{2R \sin \theta_0} \quad \cdots (5)$$

$$\frac{S_0 dz}{\sin \alpha} \quad \cdots (6)$$

FIG. 11

$$\frac{I(\alpha)\Delta\alpha}{I_0} = p\frac{L\Delta\alpha}{2R\sin\theta_0}\int_0^t dz \frac{S_0}{\sin\alpha} n\overline{Q}dv\, \rho(\phi,z)$$

$$\times \exp\left[-\mu z\left(\frac{1}{\sin\alpha}+\frac{1}{\sin\beta}\right)\right] \quad \cdots(7)$$

$$= C\Delta\alpha n\frac{1}{\sin\alpha}\int_0^t dz\, \rho(\phi,z)\exp\left[-\mu z\left(\frac{1}{\sin\alpha}+\frac{1}{\sin\beta}\right)\right] \quad \cdots(8)$$

$$C = p\frac{L}{2R\sin\theta_0} S_0 \overline{Q}dv \quad \cdots(9)$$

FIG. 13

| Design film thickness | 15 nm | 20 nm | 30 nm (standard) |
|---|---|---|---|
| H1 | 10 deg | 8.9 deg | 9.0 deg |
| H2 | 27 deg | 26 deg | 24.3 deg |
| $\eta$ | 0.093 | 0.085 | 0.15 |
| Measured film thickness t | 15.9 nm | 19.7 nm | 30.0 nm |

$$H(z) = \begin{cases} H1 \cdots (0 \leqq z \leqq \eta t) \\ H2 \cdots (\eta t < z \leqq t) \end{cases}$$

FIG. 15

$$\frac{I(\alpha)\Delta\alpha}{I_0} = C\Delta\alpha n \frac{1}{\sin\alpha} \left\{ B + \int_0^t dz\, \rho(\phi, z) \exp\left[-\mu z\left(\frac{1}{\sin\alpha} + \frac{1}{\sin\beta}\right)\right]\right\} \quad \cdots(10)$$

$$\frac{I(\alpha)\Delta\alpha}{I_0} = C\Delta\alpha n \frac{1}{\sin\alpha} \left\{ B\left(\frac{1}{\sin\alpha} + \frac{1}{\sin\beta}\right)^{-1} + \int_0^t dz\, \rho(\phi, z) \exp\left[-\mu z\left(\frac{1}{\sin\alpha} + \frac{1}{\sin\beta}\right)\right]\right\} \quad \cdots(11)$$

FIG. 16

Lorentzian function $$\rho(\phi, \xi, z) = Ga(H(z)) \left\{ 1 + 4 \left[ \frac{\phi}{H(z)} \right]^2 \right\}^{-1} \quad \cdots (12)$$

Psuedo-Voight function $$\rho(\phi, \xi, z) = \zeta G(H(z)) \exp\left[-(4 \ln 2) \left[\frac{\phi}{H(z)}\right]^2 \right] \\ + (1-\zeta) Ga(H(z)) \left\{ 1 + 4 \left[\frac{\phi}{H(z)}\right]^2 \right\}^{-1} \quad \cdots (13)$$

March-Dollase function $$\rho(\phi, \xi, z) = \frac{1}{2\pi} \left[ r(z)^2 \cos^2\phi + \frac{1}{r(z)} \sin^2\phi \right]^{-3/2} \quad \cdots (14)$$

METHOD AND APPARATUS FOR FILM THICKNESS MEASUREMENT

BACKGROUND OF THE INVENTION

1. Field of the Invention

The present invention relates to a method and an apparatus for film thickness measurement in which the thickness of a thin film is measured based on the X-ray diffraction method.

2. Description of the Related Art

It is known to use X-rays in measuring nondestructively the thickness of a thin film. The typical X-ray-related method in the determination of a film thickness is to measure an X-ray reflectance. The X-ray reflectance method can determine not only the film thickness of a single layer but also each film thickness of two laminated layers composed of different materials as disclosed in, for example, Japanese patent publication No. 10-38821 A (1998) which will be called as the first publication hereinafter.

The film thickness measurement method based on the X-ray reflectance, however, can hardly determine a film thickness in the case that (1) the density of an object thin film to be measured is close to the density of a layer adjacent to the object thin film or (2) the boundary between the object thin film and the adjacent layer has a rough surface. Assuming that a tantalum layer is deposited on a tantalum nitride layer for example, since the densities of the two layers are very close to each other, the intensity of the reflected X-ray from the boundary of Ta/TaN is weak so that it is impossible to measure the film thickness of the tantalum layer in the X-ray reflectance method.

Then, it can be planned to measure a film thickness based on the diffracted X-ray intensity with a sample whose film thickness can be hardly measured in the X-ray reflectance method. Some methods about film thickness measurement based on the diffracted X-ray intensity are known: see for example Japanese patent publication No. 4-194611 A (1992) called as the second publication hereinafter, Japanese patent publication No. 10-103942 A (1998) called as the third publication hereinafter, Japanese patent publication No. 2000-88776 A (2000) called as the fourth publication hereinafter.

The second publication introduces that, in the description of the prior art, a film thickness can be measured based on a ratio of the first intensity of a diffracted X-ray from the object thin film to be measured to the second intensity of a diffracted X-ray from the foundation layer beneath the object thin film, the ratio being called as a diffraction intensity ratio hereinafter. This method includes the steps described below. Plural object thin films are prepared with known and different film thicknesses. The diffraction intensity ratio of an object thin film to the foundation layer is measured for each object thin film. An analytical line is constructed based on the known film thicknesses of the plural object thin films and the plural diffraction intensity ratios. The film thickness of any sample can be measured based on the measured diffraction intensity ratio and the analytical line. The diffraction intensity ratio method is, however, effective only when the preferred orientation of the object thin film is known. Namely, an analytical line is constructed at first about thin films having the same known preferred orientations and thereafter a film thickness can be determined about any thin film having the same preferred orientation. The second publication says that the diffraction intensity ratio method is not usable for a thin film having an unknown preferred orientation. Consequently, the second publication proposes to use the intensity of a diffracted X-ray from the foundation layer only to measure the thickness of a thin film deposited on the foundation layer. With this method, the thickness of the object thin film can be determined out of relation to the preferred orientation of the object thin film. This method is, however, effective only under the condition that a certain extent of a diffracted X-ray can be observed from the foundation layer. If a certain extent of a diffracted X-ray can not be observed as in the case that the foundation layer is amorphous, the method proposed in the second publication is unusable.

The third publication suggests that the diffraction intensity ratio is measured using two kinds of X-ray wavelengths so that the thickness of a thin film even having a preferred orientation can be determined because the effect of the preferred orientation is cancelled. Stating in detail, the third publication points out that even when the preferred orientation of the sample is changed, there is no relation between the diffracted X-ray intensity and the amount of a film deposited. There are used two kinds of X-ray wavelengths, e.g., the characteristic X-ray of Cr and the characteristic X-ray of Cu, to detect the two intensities of diffracted X-rays in the same direction and from the same lattice spacing. The diffraction intensity ratio of the two intensities depends upon the amount of deposition because the effect of the preferred orientation is cancelled. If an analytical line is constructed in advance about the relationship between the diffracted X-ray intensity and the amount of deposition, the amount of deposition can be determined with the measurement of the diffraction intensity ratio, noting that the relationship would become a curved line. It is noted in this method that it is necessary, for making an analytical line, to prepare plural object thin films having known and different film thicknesses and to measure the diffraction intensity ratio among the object thin films with the use of two kinds of X-ray wavelengths.

The fourth publication discloses that: the diffracted X-ray intensities are measured for both of a sample having a thin film thereon and another sample from which a thin film has been removed; a variation curve of the diffraction intensity ratio with an incident angle being changed is determined, the curve becoming a measured rocking curve; a theoretical rocking curve containing a film thickness and a film density as parameters is produced; and the film thickness and the film density can be determined so that the theoretical rocking curve can approach the measured rocking curve as closely as possible. The fourth publication is deeply pertinent to the present invention in view of the use of a parameter fitting operation about the diffracted X-ray intensity. It is necessary in this method, however, that: the diffracted X-ray intensity is measured for a sample having a thin film deposited thereon; the thin film is removed; and then the diffracted X-ray intensity is measured again for the sample from which the thin film has been removed. Accordingly, this method can not be said to be the nondestructive measurement. Since the greatest advantage of the X-ray-using film thickness measurement method is that it is the nondestructive measurement, the method disclosed in the fourth publication, which must have the step of removing the thin film, would lose the greatest advantage with the use of X-ray.

Noting that the present invention has a feature, which is one of the features of the invention, of using a theoretical formula about the diffracted X-ray intensity in consideration of the orientation density distribution function, the prior art involved with this feature is known and disclosed in H. Toraya, H. Hibino, T. Ida and N. Kuwano, Quantitative basis for the rocking-curve measurement of preferred orientation in polycrystalline thin films, (2003), Journal of Applied Crystallography, 36, p. 890–897 which will be called as the fifth publication.

The film thickness measurement methods disclosed in the second to the fourth publications have the problems described below. The method of the second publication is to measure the thickness of the object thin film based on the intensity of a diffracted X-ray from the foundation layer for the purpose of eliminating the effect of the preferred orientation of the object thin film. This method is effective only under the condition that a certain extent of a diffracted X-ray can be observed from the foundation layer, and accordingly the method is unusable in the case that the foundation layer is amorphous. Explaining with an example, the method of the second publication is unusable for measuring the film thickness of a tantalum layer which is deposited on a tantalum nitride layer, because the tantalum nitride layer is amorphous.

The method of the third publication suggests the measurement of the thickness of the object thin film based on the diffraction intensity ratio which is obtained with the use of two kinds of X-ray wavelengths. This method has problems that (1) an X-ray source which can generate two kinds of X-ray wavelengths must be prepared, for instance, an X-ray tube which can generate the characteristic X-ray of Cr and another X-ray tube which can generate the characteristic X-ray of Cu and (2) an analytical line indicating the relationship between the diffraction intensity ratio and the film thickness must be created beforehand, that is, the prior measurement operation must be carried out for plural object thin films having known and different film thicknesses.

The method of the fourth publication has problems that (1) the diffracted X-ray intensity must be measured again for the sample from which the thin film has been removed after the measurement of the diffracted X-ray intensity for the sample having the thin film deposited thereon, the method being not the nondestructive measurement and (2) a reliable film thickness would not be expected for a sample having a preferred orientation, because the method does not take account of the specific theory for the sample having a preferred orientation.

SUMMARY OF THE INVENTION

The present invention has been devised to solve the above-described problems. It is an object of the present invention to provide a method of measuring a film thickness in which (1) a film thickness can be measured even for a thin film whose thickness can not be measured based on the X-ray reflectance method as in the case that there exists the adjacent layer having a density which is close to the density of the object thin film or the boundary between the adjacent layer and the object layer has a rough surface, (2) there are no restrictions on the material of the foundation layer, (3) it is enough to use a single X-ray wavelength, (4) a specific procedure for creating an analytical line is not wanted, that is, it is unnecessary to prepare operation needing plural object thin films having known and different film thicknesses, (5) a film thickness can be determined with higher reliability even for a thin film having a preferred orientation, and (6) a film thickness can be determined using the nondestructive measurement.

A method of measuring a film thickness according to the present invention is characterized in that a film thickness is determined with the use of a parameter fitting operation between a measured rocking curve and a theoretical rocking curve which is calculated in consideration of the orientation density distribution function, and thus the present invention comprises the steps of (a) preparing a thin film made of a polycrystalline material; (b) assuming an orientation density distribution function $\rho$ which is axisymmetric about a normal direction of a surface of the thin film, the orientation density distribution function $\rho$ being a function of an angle $\phi$ at which a normal of a measurement lattice plane of a crystallite of the thin film is inclined to a normal of the surface of the thin film, and the orientation density distribution function $\rho$ containing at least one characteristic parameter characterizing a form of the function; (c) allowing an X-ray to be incident upon the surface of the thin film at an incident angle $\alpha$, measuring an intensity of a diffracted X-ray which is reflected at the measurement lattice plane of the thin film, and determining a variation of the intensity of the diffracted X-ray from the measurement lattice plane with the incident angle $\alpha$ being changed to obtain a measured rocking curve; (d) calculating a theoretical diffracted X-ray intensity, based on (i) a scale factor which is predetermined for a standard sample having a known film thickness, (ii) the orientation density distribution function $\rho$ and (iii) a film thickness t of the thin film, to obtain a theoretical rocking curve about a variation of the intensity of the diffracted X-ray from the measurement lattice plane with the incident angle $\alpha$ being changed; and (e) carrying out a parameter fitting operation in which the characteristic parameter and the film thickness t are adjusted so that the theoretical rocking curve can approach the measured rocking curve as closely as possible, whereby the film thickness t is determined.

The present invention enables the film thickness measurement for thin films having different preferred orientations based on the X-ray diffraction method, especially even for a sample whose film thickness can not be measured based on the X-ray reflectance method.

The orientation density distribution function may be a Gaussian function, a Lorentzian function, a pseudo-Voight function or a March-Dollase function. In the case of the Gaussian function, if a single full-width-at-half-maximum (FWHM) is insufficient for good fitting, the FWHM H of the Gaussian function is allowed to depend upon a depth z measured from the surface of the thin film. The FWHM H may be equal to a constant value H1 when z is in a range between zero and $\eta t$, where $\eta$ is in a range between zero and 1, and the FWHM H may be equal to another constant value H2 when z is in a range between $\eta t$ and t. In this case, the parameter fitting operation is carried out with adjusting the three characteristic parameters H1, H2 and $\eta$ and the film thickness t.

An apparatus for measuring a film thickness according the present invention is to measure the thickness of a thin film made of a polycrystalline material, and the apparatus comprises: (a) a memory for storing an orientation density distribution function $\rho$ which is axisymmetric about a normal direction of a surface of the thin film, the orientation density distribution function $\rho$ being a function of an angle $\phi$ at which a normal of a measurement lattice plane of a crystallite of the thin film is inclined to a normal of the surface of the thin film, and the orientation density distribution function $\rho$ containing at least one characteristic parameter characterizing a form of the function; (b) rocking curve measurement means for producing a measured rocking curve in which an X-ray is incident upon the surface of the thin film at an incident angle $\alpha$, an intensity of a diffracted X-ray which is reflected at the measurement lattice plane of the thin film is measured, and a variation of the intensity of the diffracted X-ray from the measurement lattice plane with the incident angle α being changed is determined; (c) theoretical calculation means for producing a theoretical rocking curve about a variation of the intensity of the diffracted X-ray from the measurement lattice plane with the incident angle α being changed in which a theoretical diffracted X-ray intensity is calculated based on (i) a scale factor which is predetermined for a standard sample having a known film thickness, (ii) the orientation density distribution function ρ and (iii) a film thickness t of the thin film; and (d) film thickness determination means for determining the film thickness t in which a parameter fitting operation is carried out in a manner that the characteristic parameter and the film thickness t are adjusted so that the theoretical rocking curve can approach the measured rocking curve as closely as possible.

The method and apparatus according to the present invention have the advantages that (1) the thickness of an object thin film can be measured even when there exists the adjacent layer having a density which is close to the density of the object thin film, (2) the thickness of an object thin film can be measured even when the boundary between the adjacent layer and the object thin film has a rough surface, (3) a film thickness can be measured even for a thin film having a relatively large thickness which can not be measured based on the X-ray reflectance method, (4) reliability of the measured film thickness is increased in the film thickness measurement based on the X-ray diffraction method in consideration of the preferred orientation of the thin film, and (5) there are no restrictions on the material of the foundation layer in the film thickness measurement based on the X-ray diffraction method.

BRIEF DESCRIPTION OF THE DRAWINGS

FIG. 8 shows equations which are in relation to an orientation density distribution function;

FIG. 10 shows an equation and terms which are in relation to the diffracted X-ray intensity;

FIG. 11 shows other equations which are in relation to the diffracted X-ray intensity;

FIG. 13 is a list of the measurement results;

FIG. 15 shows theoretical formulas in consideration of the background; and

FIG. 16 shows equations of other orientation density distribution functions.

DETAILED DESCRIPTION OF THE PREFERRED EMBODIMENTS

Figure 1:
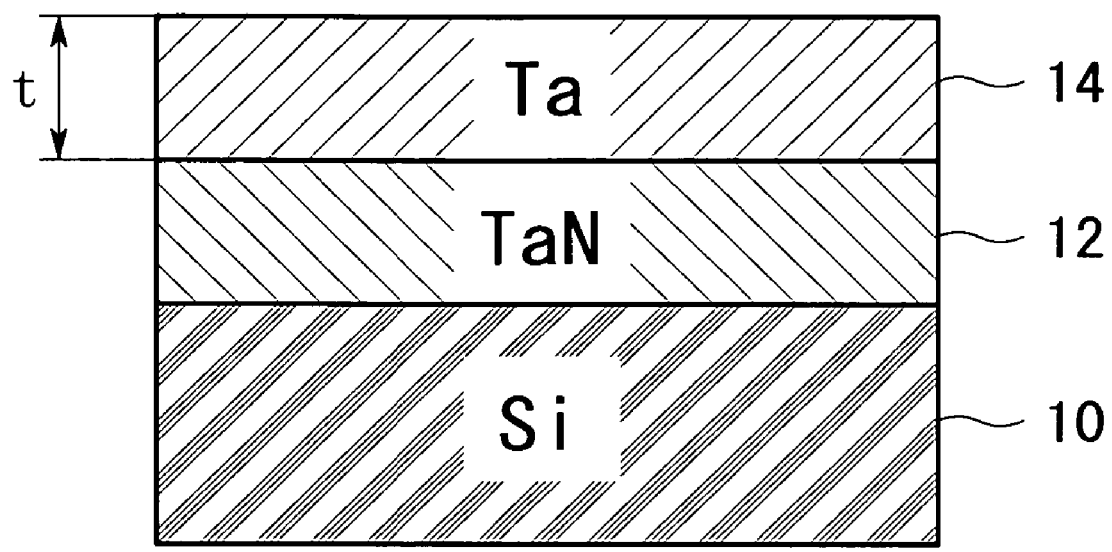
FIG. 1 is a sectional view of a sample.

Embodiments of the present invention will now be described below with reference to the drawings. Referring to FIG. 1 showing a sample in section, a tantalum nitride layer 12 is deposited on a silicon substrate 10 and a tantalum layer 14 is further deposited on the tantalum nitride layer 12. The multilayer film composed of Ta and TaN may be used as a diffusion barrier layer between an insulating layer and a copper wiring layer in the case that the copper wiring layer is deposited on the insulating layer in the manufacturing process of the semiconductor device. The present invention is usable effectively in estimating the film thickness of the tantalum layer in the multilayer of Ta/TaN. An embodiment of the present invention described below is to measure the film thickness of the above-described tantalum layer based on the X-ray diffraction method.

At first, it will be verified whether or not a film thickness can be successfully measured based on simply the peak intensity or the integral intensity of a diffracted X-ray without consideration of the preferred orientation of the tantalum layer. A multilayer of Ta/TaN whose total thickness is about 30 nm is prepared as a sample. A diffraction peak profile of the sample was measured in the ordinary θ/2θ scan method, resulting in the observation of a diffraction peak of Si(004) at near 69 degrees in 2θ and another diffraction peak of Ta(110) at near 38 degrees in 2θ as major peaks in a range between 20 to 80 degrees in 2θ. The tantalum nitride layer is contemplated to be amorphous and thus any clear diffraction peaks were not observed in connection with the tantalum nitride layer. It is understood, from the diffraction measurement result, that the normal direction of the Ta(110) plane was strongly oriented in the normal direction of the surface of the sample. It was attempted to determine the film thickness of the tantalum layer based on the diffraction peak of Ta(110).

It is expected that the more the film thickness of the tantalum layer increases, the more the intensity of the diffraction peak increases under the condition that the film thickness is in a range in which an X-ray can reach the bottom of the tantalum layer, less than 1 μm for example. Then, three samples of tantalum layers were prepared for experiments described below, the film thicknesses being designed to 30 nm, 20 nm and 15 nm. The three kinds of thicknesses can be set to the predetermined values with the control of the film deposition process, the film thicknesses having sufficient accuracy in evaluating the film thickness measurement method. The film thickness set to the predetermined value in this process will be called as a design film thickness hereinafter.

In connection with the diffraction peak of Ta(110), the diffraction peak profile was measured in the θ/2θ scan method and its peak intensity and its integral intensity were determined for each of the three kinds of the film thicknesses. For the tantalum layer sample with 30 nm in film thickness, the peak intensity is expressed by Ip30 and the integral intensity is expressed by Ii30. Similarly, for the sample with 20 nm, the peak intensity is Ip20 and the integral intensity is Ii20. For the sample with 15 nm, the peak intensity is Ip15 and the integral intensity is Ii15. In the graph shown in FIG. 2, relative peak intensities and relative integral intensities are plotted on the ordinate against design film thicknesses of the tantalum layer on the abscissa. The relative peak intensities become Ip30/Ip30, Ip20/Ip30 and Ip15/Ip30 respectively on the basis of the peak intensity Ip30 of the standard sample with 30 nm. The relative integral intensities become Ii30/Ii30, Ii20/Ii30 and Ii15/Ii30 respectively on the basis of the integral intensity Ii30 of the standard sample with 30 nm. If the peak intensity is proportional to the film thickness, the relative peak intensities for the three kinds of the film thicknesses are expected to appear on the straight line 40 connecting the origin and Ip30/Ip30. The relative peak intensities are, however, far out of the straight line 40. Accordingly, the film thickness can not be determined based on the peak intensity on the assumption of the proportional relationship between the peak intensity and the film thickness. Similarly, if the integral intensity is proportional to the film thickness, the relative integral intensities for the three kinds of the film thicknesses are expected to appear on the straight line 40. The relative integral intensities also are, however, far out of the straight line 40. Accordingly, the film thickness can not be determined also based on the integral intensity on the assumption of the proportional relationship between the integral intensity and the film thickness.

Even if the peak intensity or the integral intensity is not proportional to the film thickness, there is the possibility that any analytical line about the relationship therebetween can be constructed and the film thickness might be determined based on the analytical line. However, when the preferred orientation is changed, the peak intensity and the integral intensity also are changed even with the same film thickness, the analytical line being not effective under the condition of unknown preferred orientation of the thin film.

It is contemplated generally that when the thickness of the thin film is changed, the preferred orientation of the crystallite of the thin film also is changed. When the preferred orientation is changed with the film thickness, it would be impossible to precisely determine the film thickness based on the peak intensity or the integral intensity. Consequently, the present invention is to evaluate quantitatively the preferred orientation of the crystallite and to calculate theoretically the diffracted X-ray intensity and to determine the parameters of the orientation density distribution function and the film thickness so that the theoretical rocking curve can approach the measured rocking curve as closely as possible, resulting in that the thickness of the thin film can be precisely evaluated based on the X-ray diffraction method.

Figure 3:
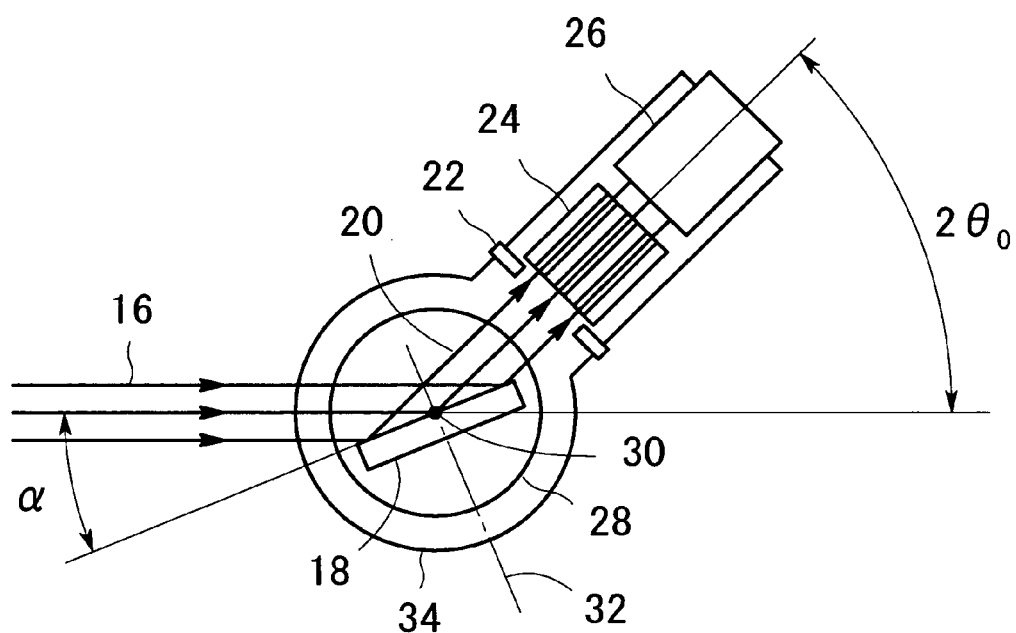
FIG. 3 is a plan view of an embodiment of an X-ray diffraction apparatus for use in carrying out the present invention.

First, a method for determining a measured rocking curve will be described. FIG. 3 is a plan view of an embodiment of an X-ray diffraction apparatus for use in carrying out the present invention. The X-ray diffraction apparatus corresponds to rocking curve measurement means for producing a measured rocking curve in the present invention. An incident X-ray 16 consisting of a parallel X-ray beam is allowed to be incident upon the surface of a sample 18 at an incident angle α. The diffracted X-ray 20 which is reflected at the sample 18 passes through a receiving slit 22 and a Soller slit 24, and is detected by an X-ray detector 26. Thus, this X-ray diffraction apparatus is operated in a parallel beam method.

The receiving system (the receiving slit 22, the Soller slit 24 and the X-ray detector 26) is arranged at an angle $2\theta_0$ with respect to the incident X-ray 16. The Bragg angle, which depends on the wavelength of the incident X-ray 16, of the measurement lattice plane of the sample 18 is $\theta_0$. The sample 18 is placed on a sample rotary stage 28. The sample rotary stage 28 can be rotated around the center 30, which is perpendicular to the paper sheet of FIG. 3, of a goniometer. Moreover, the sample 18 can be rotated around a horizontal axis of rotation 32 which is perpendicular to the center 30 of the goniometer, that is, the sample 18 can take an in-plane rotation. The receiving system is placed on the detector rotary stage 34 which can be also rotated around the center 30 of the goniometer.

Figure 4A:
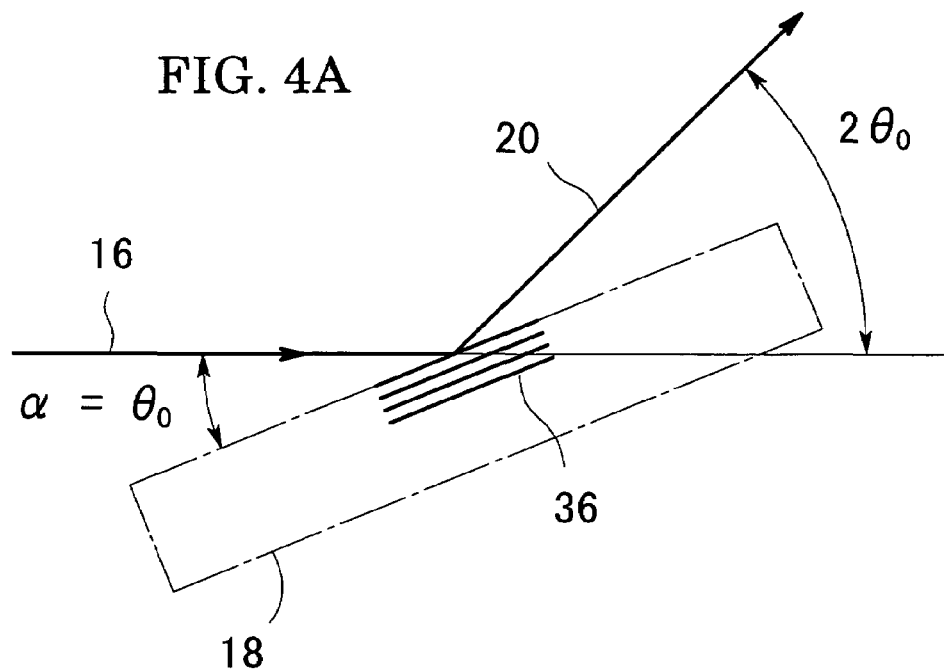
FIGS. 4A and 4B illustrate the different states in which an X-ray is diffracted with an incident angle being changed.
Figure 4B:
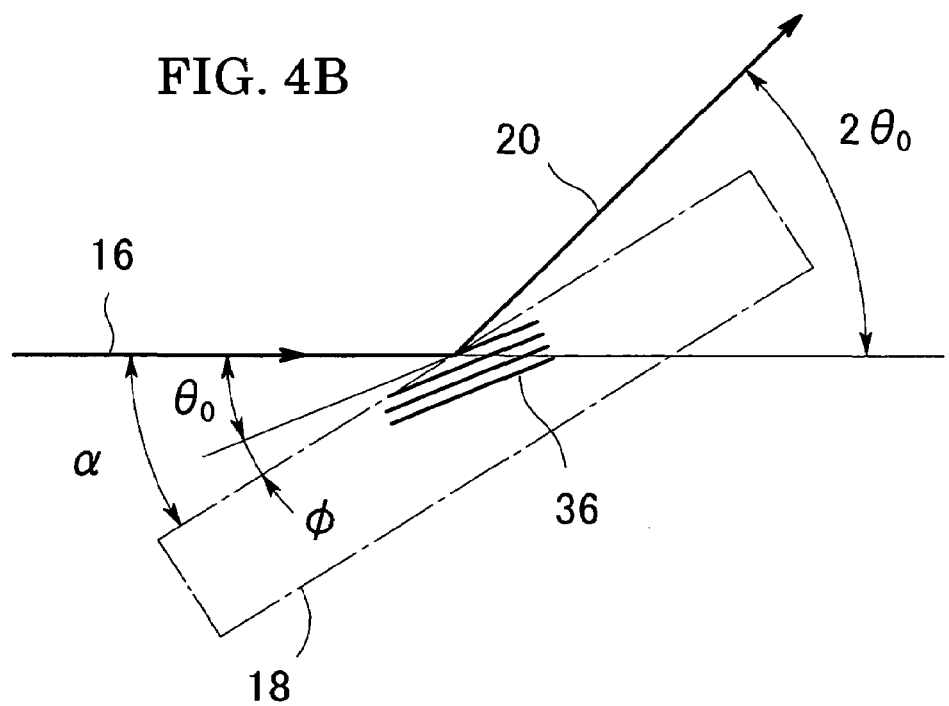

The above-mentioned Bragg angle $\theta_0$ can be decided by selecting the measurement lattice plane of the sample 18 and the wavelength of the X-ray used. In this embodiment, the measurement lattice plane is Ta(110) and the used X-ray is a CuKα ray, the Bragg angle $\theta_0$ becoming about 18.9 degrees. Referring to FIG. 4A, when the incident angle α is equal to $\theta_0$, the measurement lattice plane 36, which contributes to the diffraction, is parallel to the surface of the sample 18. Naturally, the normal of the measurement lattice plane 36 is parallel to the normal of the sample surface. In other words, only the crystallite that has the measurement lattice plane parallel to the sample surface contributes to the diffraction. The diffracted X-ray 20 from the above-mentioned crystallite will be detected. On the other hand, in FIG. 4B, when the sample 18 is rotated by an angle φ, that is, the incident angle α=$\theta_0$+φ, only the crystallite whose measurement lattice plane 36 is inclined to the sample surface by an angle φ contributes to the diffraction. As described above, when the detector is fixed at the position of $2\theta_0$ while the sample 18 is rotated, the incident angle α is changed. As a result, there can be obtained information on the diffracted X-ray intensity for the different crystallites which correspond to respective inclination angles φ, that is, different crystallites oriented by different angles φ with respect to the sample surface.

In the present invention, since the orientation density distribution function ρ is assumed to be axisymmetric about the normal direction of the sample surface, the sample is allowed to take an in-plane rotation during the measurement of the diffracted X-ray intensity. Thereby, the theoretical rocking curve and the measurement rocking curve can be compared with each other. It is to be noted that if the preferred orientation of a sample is expected to be axisymmetric actually, the in-plane rotation of the sample may be omitted.

Figure 5:
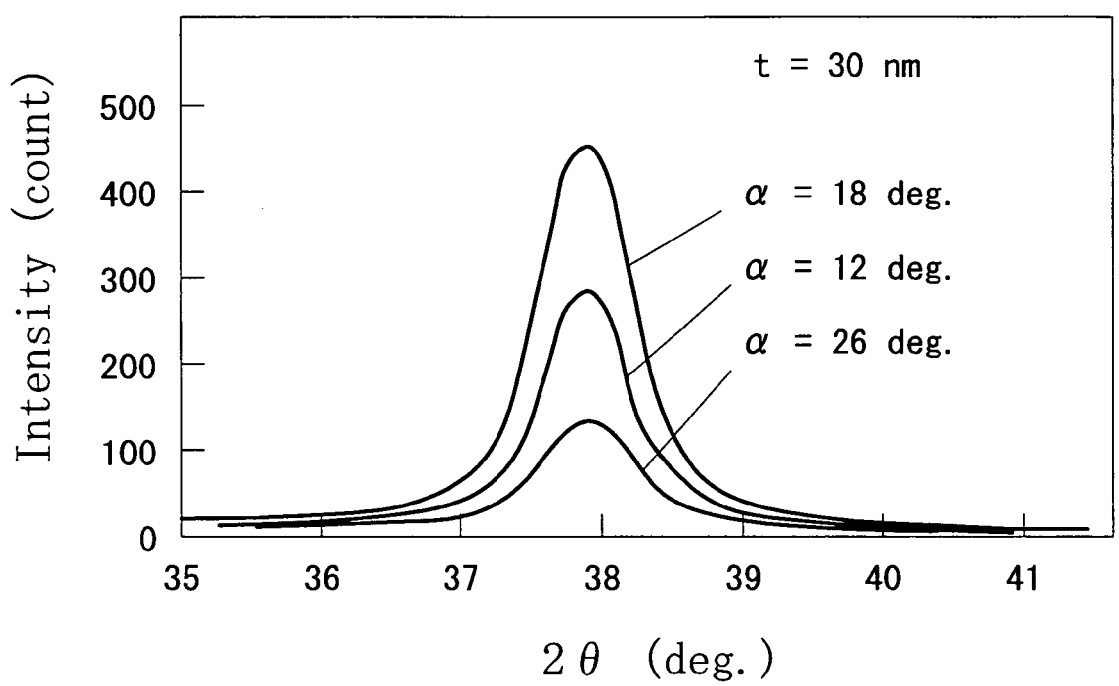
FIG. 5 is a graph showing peak profiles of diffracted X-rays.
Figure 6:
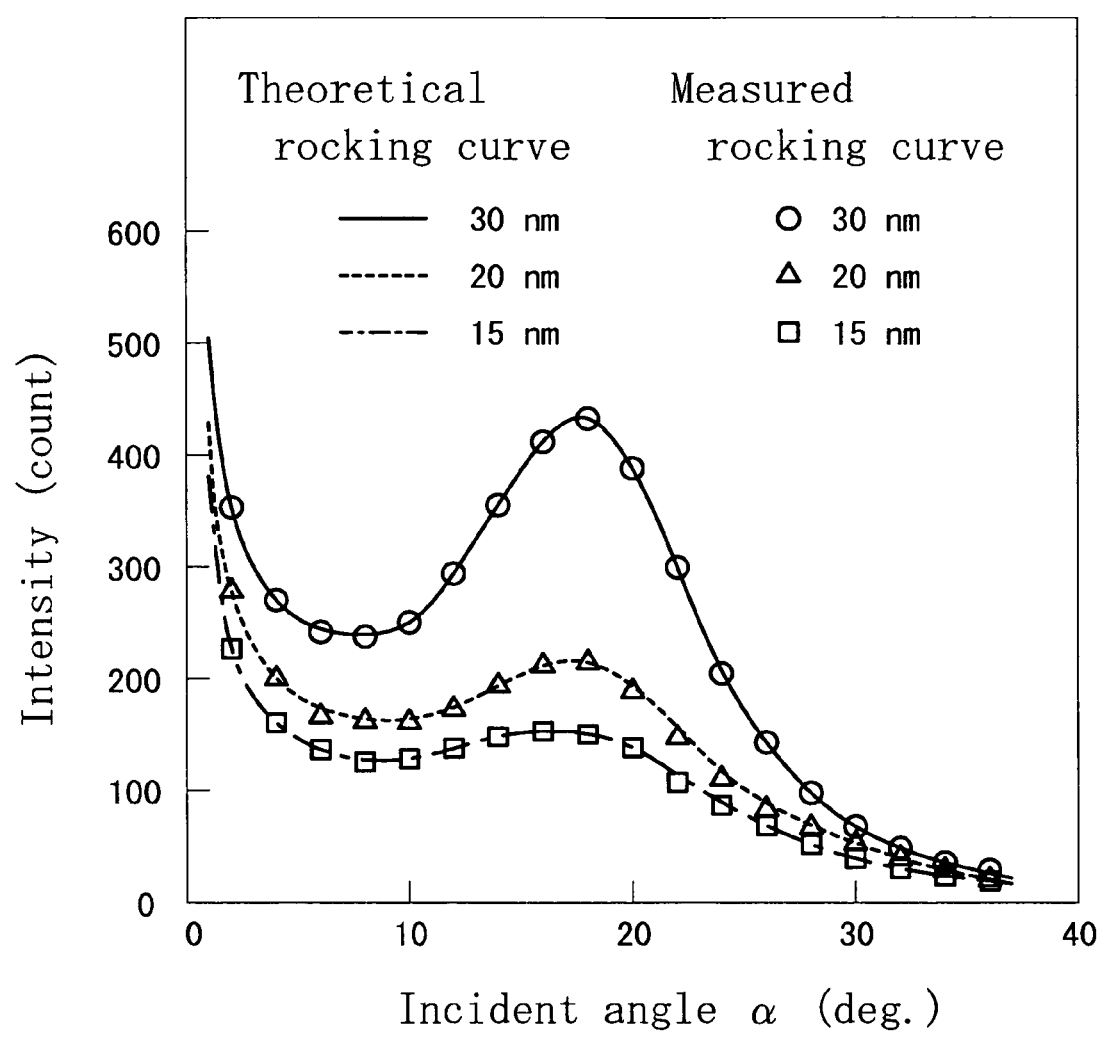
FIG. 6 is a graph showing theoretical rocking curves superimposed on measured rocking curves.

As described above, the diffracted X-ray intensity I is measured with the incident angle α being changed while the position of the detector is fixed at $2\theta_0$, so that an α–I rocking curve can be obtained. To accurately determine the diffracted X-ray intensity, it is preferable to obtain the integral intensity of a diffraction peak as described below. That is, the receiving system is scanned around the angle $2\theta_0$ while a certain incident angle α is fixed, so that a peak profile as shown in FIG. 5 can be obtained. FIG. 5 is a graph showing Ta(110) peak profiles measured for the tantalum layer in FIG. 1 with 30 nm in thickness. The peak profiles shown in the graph can be obtained by scanning the receiving system around $2\theta_0$ while the incident angle α is fixed to 12, 18 or 26 degrees for example. An accurate diffracted X-ray intensity can be obtained by determination of the area of the peak profile, that is, determination of the integral intensity. Each of the measurement points composing a measured rocking curve shown in FIG. 6 is obtained in a manner that the peak profile as shown in FIG. 5 is measured for the tantalum layer with 15 nm, 20 nm or 30 nm in film thickness t at two-degree intervals in α in a range between 2 and 36 degrees in α and thereafter the integral intensity of the peak profile is determined for the plot in FIG. 6. Namely, one peak profile shown in FIG. 5 corresponds to one measurement point in a measured rocking curve shown in FIG. 6, a set of the measurement points making one rocking curve. It should be noted that the curved lines in FIG. 6 are not the measured rocking curves but theoretical rocking curves which are allowed to approach the measured rocking curves as closely as possible.

Figure 7:
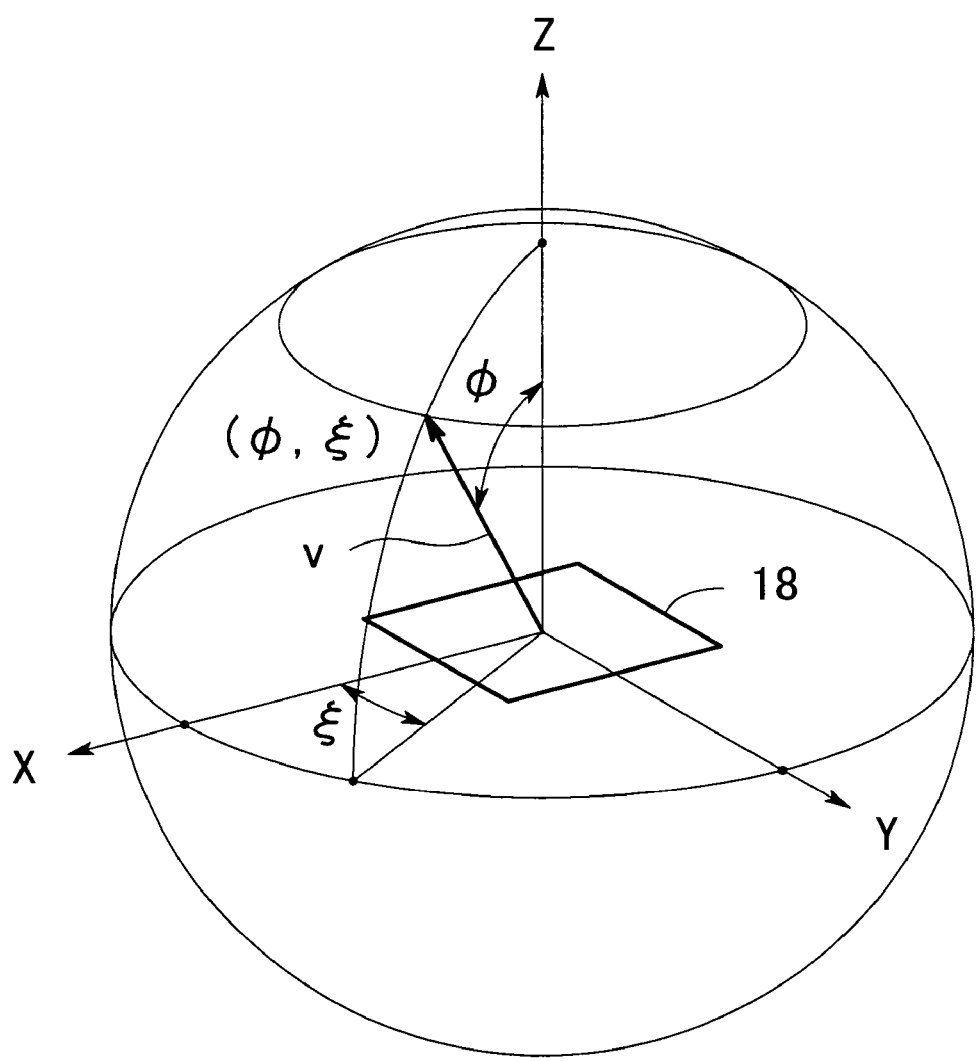
FIG. 7 is a perspective view of the normal vector v of the measurement lattice plane of a crystallite in the polar coordinate system.

Next, a method of determining the theoretical rocking curve will be described. FIG. 7 is a perspective view of the normal vector v of the measurement lattice plane of a crystallite in the polar coordinate system. The X-Y plane is assumed to be on the surface of the sample 18, and the Z-axis extends in the normal direction of the sample surface. The normal vector v of the measurement lattice plane of the crystallite can be expressed by spherical coordinates $(\phi,\xi)$. The angle $\phi$ is an angle with which the normal vector v is inclined from the Z-axis which is the normal of the sample surface. The angle $\xi$ is an azimuth from the X-axis when the normal vector v is projected onto the X-Y plane.

In general, the orientation density distribution function $\rho$ of a crystallite having a normal vector v is a function of $\phi$ and $\xi$. Additionally, the function $\rho$ is assumed to depend on the depth z in the object thin film, i.e., $\rho=\rho(\phi,\xi,z)$. The normalizing condition of the orientation density distribution function $\rho$ is expressed by equation (1) in FIG. 8. Assuming that the functional form of $\rho$ is an axisymmetric about the Z-axis, the $\rho$ does not depend on $\xi$ and thus becomes a function of $\phi$ and z only.

Figure 9:
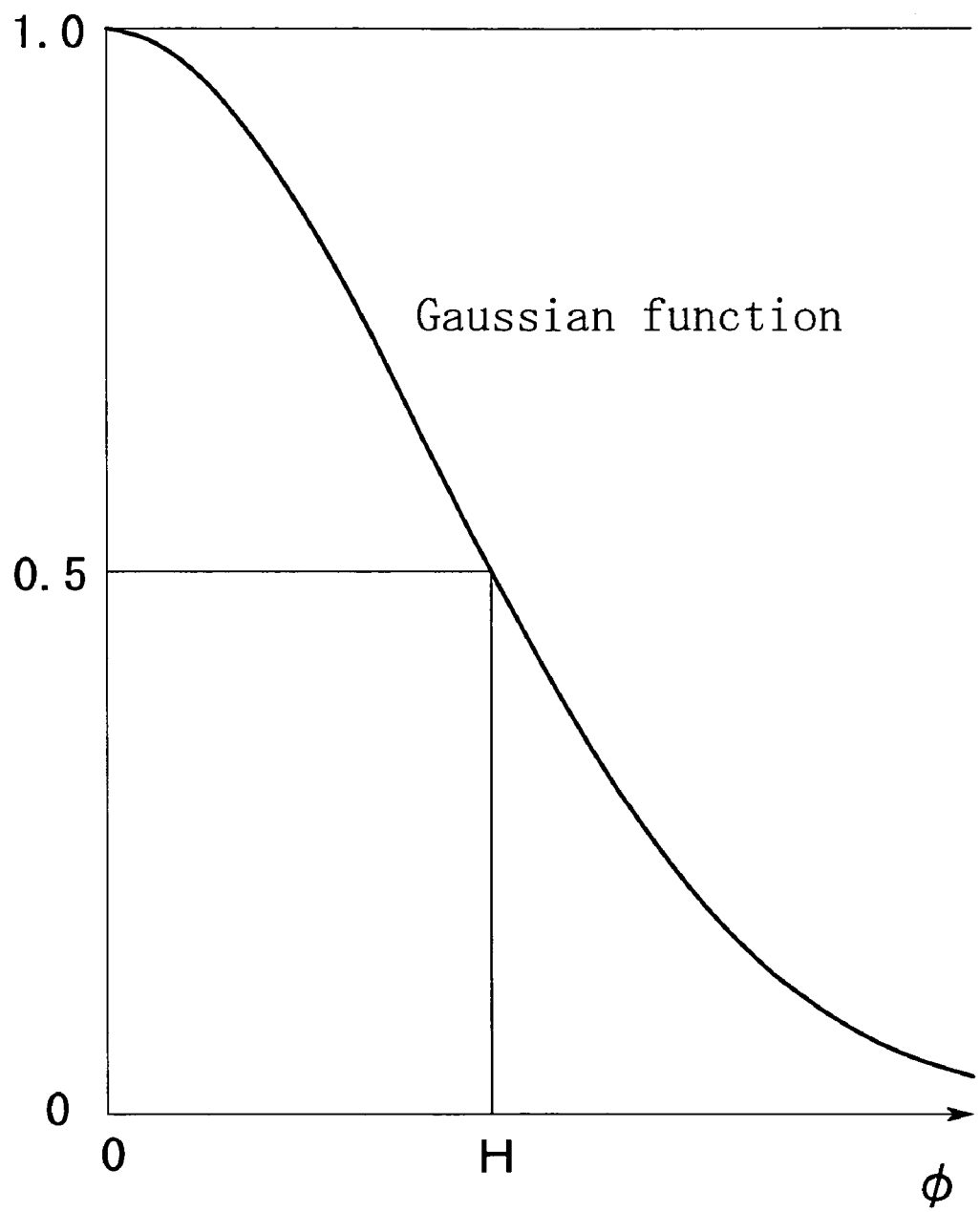
FIG. 9 is a graph showing a Gaussian function.

In this embodiment, the orientation density distribution function $\rho$ is assumed to be the Gaussian function which is expressed by equation (2) in FIG. 8. The symbol G in equation (2) is a normalizing factor, which can be calculated by equation (3). The symbol H(z) is the full-width-at-half-maximum of the Gaussian function, and has a dimension of angle. The H is assumed to depend on the depth z and is a characteristic parameter which characterizes the functional form of the Gaussian function. Accordingly, when the H is determined, the functional form of $\rho$ is determined. When the functional form is determined, the theoretical diffracted X-ray intensity can be calculated as described below. FIG. 9 is a graph showing the Gaussian function. The functional form of the orientation density distribution function $\rho$ is to be stored in a memory device of the thin film measurement apparatus and is used in a computer program calculating the theoretical rocking curve.

The scattering power Q of the $2\theta_0$-diffraction plane per unit volume is expressed by equation (4) in FIG. 10, in which $N_0$ is the number of unit cells per unit volume, $\lambda$ is an X-ray wavelength, F(hkl) is a structure factor, e and m are the charge and the mass of an electron, and c is a light velocity in a free space. When the average volume of a crystallite is expressed by dv with a horizontal line thereabove, it multiplied by Q provides the scattering power per one crystallite. The incident angle $\alpha$ of an incident X-ray is expressed by $\alpha=\theta_0+\phi$, and the exit angle $\beta$ of a diffracted X-ray is expressed by $\beta=\theta_0-\phi$. The solid angle covering the receiving slit 22 is expressed by term (5) in FIG. 10. The volume, of the object thin film, irradiated by an incident X-ray having a cross-sectional area $S_0$ is expressed by term (6) in FIG. 10. In consideration of the explanation above, the diffracted X-ray intensity I $(\alpha)\Delta\alpha$ about the X-ray which passes through the receiving slit 22, with a slit length L, disposed at a distance R from the sample and is detected by the X-ray detector 26 is expressed by equation (7) in FIG. 11, noting that the intensity $I(\alpha)\Delta\alpha$ is divided by the incident X-ray intensity $I_0$. In equation (7), p is the multiplicity of reflection. The orientation density distribution function $\rho$ is assumed not to depend on $\xi$ and thus is $\rho(\phi,z)$ accordingly. In equation (7), the constant part which does not depend on the film thickness t and the incident angle $\alpha$ can be substituted by a scale factor C, and then equation (7) becomes equation (8). The scale factor C is expressed by equation (9). The film thickness measurement apparatus is equipped with a computer program for calculating equation (8) so as to determine a theoretical diffracted X-ray intensity. The function of the computer program corresponds to the theoretical calculation means of the film thickness measurement apparatus according to the present invention.

In equation (8), when the orientation density distribution function $\rho$ is assumed to be the Gaussian function which is expressed by equation (2) in FIG. 8, the theoretical diffracted X-ray intensity can be changed by adjusting the FWHM H(z) and the film thickness t, the H(z) being the characteristic parameter of the Gaussian function.

Figure 12:
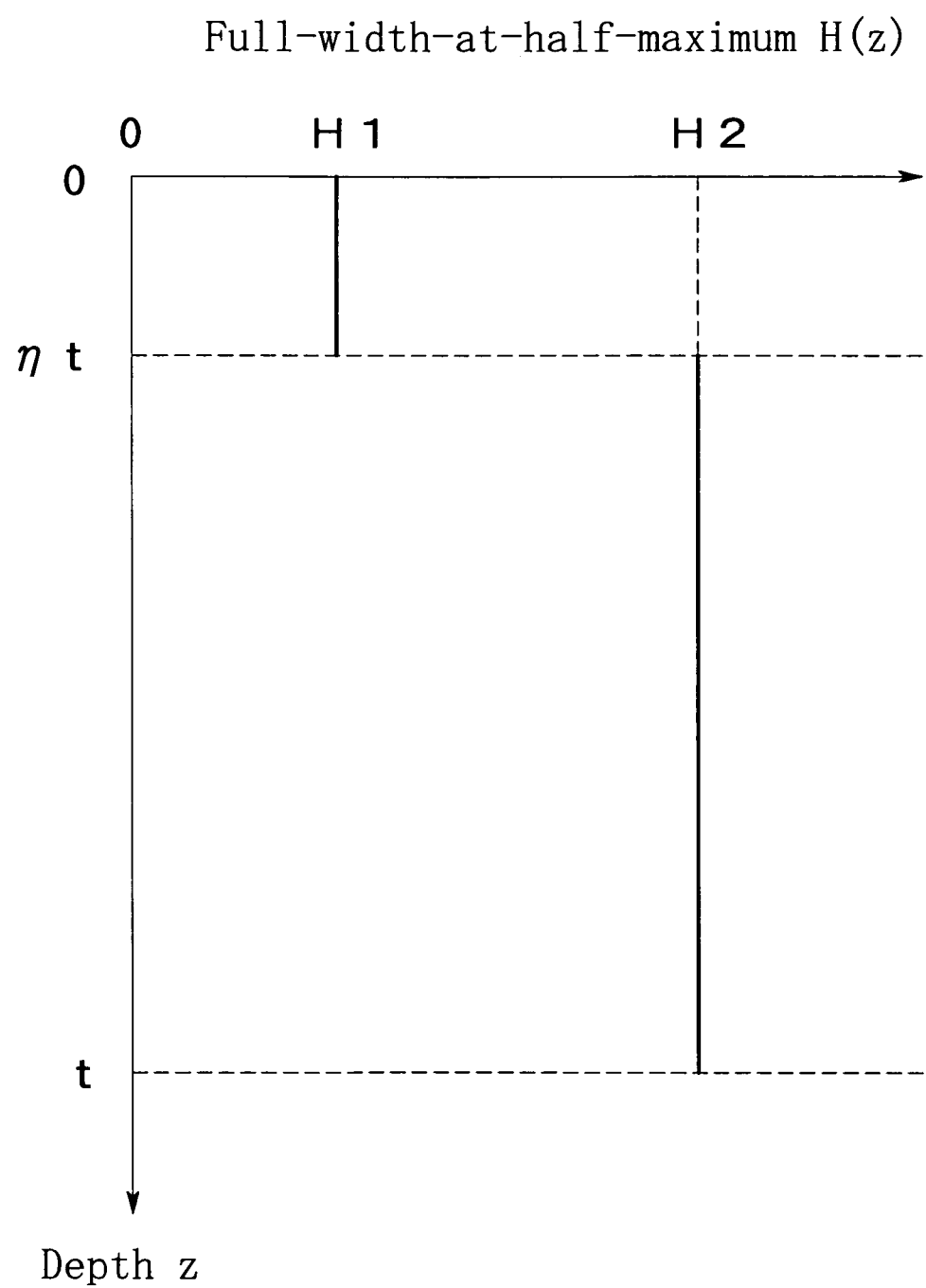
FIG. 12 a graph showing the full-width-at-half-maximum H(z) of the Gaussian function.

FIG. 12 shows assumption about the function form of the FWHM H(z) of the Gaussian function. It is assumed for a thin film having a thickness t that the FWHM is equal to a constant value H1 when the depth z is in a range between zero and $\eta t$, where $\eta$ is in a range between zero and 1, whereas the FWHM is equal to another constant value H2 when z is in a range between $\eta t$ and t, i.e., it is the two-layer model. The two-layer model is to use three characteristic parameters H1, H2 and $\eta$ for defining the orientation density distribution function $\rho$.

Next, it will be attempted to allow the theoretical rocking curve to be fitted to the measured rocking curve with the use of the tantalum thin film having a design film thickness of 30 nm as the standard sample. The intensity of equation (8) in FIG. 11 is calculated with the above-described characteristic parameters H1, H2 and $\eta$ being changed. The parameter fitting operation is carried out in a manner that the parameters H1, H2 and $\eta$ are changed so that the calculated intensity can approach the respective measurement points of 30 nm shown in FIG. 6 as closely as possible, noting that the film thickness t in equation (8) in FIG. 11 is substituted by the design film thickness of 30 nm. Further, the scale factor C can be adjusted to shift the total intensity of the theoretical rocking curve. As has been described above, the curved shape of the theoretical rocking curve can be changed by adjusting the parameters H1, H2 and $\eta$, whereas the total intensity can be changed by adjusting the scale factor C. The parameters H1, H2 and $\eta$ were determined so that the theoretical rocking curve can approach the measured rocking curve of 30 nm as closely as possible. The resultant theoretical rocking curve is the solid curved line shown in FIG. 6. The resultant values of H1, H2 and $\eta$ appear, in FIG. 13, in the column of 30 nm of the table: H1 is 9 degrees, H2 is 24.3 degrees and $\eta$ is 0.15. The scale factor C was determined at the same time and is usable in the parameter fitting operation for other design film thicknesses of 15 nm and 20 nm.

Next, a similar parameter fitting operation was carried out for the tantalum thin film having the design film thickness of 20 nm. The film thickness t shown in equation (8) in FIG. 11 is assumed to be unknown this time, and the scale factor C is substituted by the value which has been determined for the sample of 30 nm. The parameters H1, H2 and $\eta$ and the film thickness t were adjusted so that the theoretical rocking curve can approach the measured rocking curve of 20 nm as closely as possible, the resultant theoretical rocking curve being the broken curved line shown in FIG. 6. The resultant values of H1, H2 and $\eta$ appear, in FIG. 13, in the column of 20 nm of the table: H1 is 8.9 degrees, H2 is 26 degrees and $\eta$ is 0.085. The parameter fitting operation brought a measured film thickness t of 19.7 nm, which is very close to the design film thickness of 20 nm.

Next, a similar parameter fitting operation was carried out for the tantalum thin film having the design film thickness of 15 nm. The film thickness t included in equation (8) in FIG. 11 is assumed to be unknown too, and the scale factor C is substituted by the value which has been determined for the sample of 30 nm. The parameters H1, H2 and η and the film thickness t were determined so that the theoretical rocking curve can approach the measured rocking curve of 15 nm as closely as possible, the resultant theoretical rocking curve being the chain curved line shown in FIG. 6. The resultant values of H1, H2 and η appear, in FIG. 13, in the column of 15 nm of the table: H1 is 10 degrees, H2 is 27 degrees and η is 0.093. A measured film thickness was 15.9 nm, which is very close to the design film thickness of 15 nm as well.

As has been described above, if the film thickness is assumed to be unknown for the samples which actually in turn have the design film thickness of 20 nm and 15 nm, measured film thicknesses can be obtained using the scale factor C, the resultant measured film thickness being 19.7 nm and 15.9 nm. It would be understood from the results that the film thickness measurement method according to the present invention is effective without large errors. Furthermore, the preferred orientation of the thin film can be evaluated quantitatively with the characteristic parameters H1, H2 and η which are to be determined at the same time. As can be seen from the table in FIG. 13, when the film thickness is changed, the parameters H1, H2 and η pertinent to the preferred orientation also are changed.

Now, the experimental results described above are summarized below. The scale factor C can be determined in a manner that the tantalum thin film having a design film thickness of 30 nm is used as the standard sample and the parameter fitting operation is carried out so that the theoretical rocking curve can be fitted to the measured rocking curve. Next, for the tantalum thin film having an unknown film thickness, the characteristic parameters of the orientation density distribution function and the unknown film thickness t can be determined in a manner that the scale factor C is substituted by the determined value and the parameter fitting operation is carried out so that the theoretical rocking curve can be fitted to the measured rocking curve as closely as possible. As a result, the film thickness of the tantalum thin film on the tantalum nitride layer can be determined based on the X-ray diffraction method, and at the same time the preferred orientation of the tantalum thin film can be evaluated quantitatively. The parameter fitting operation can be realized with the computer program whose function can be said to correspond to the film thickness determination means of the film thickness measurement apparatus according to the present invention.

Figure 2:
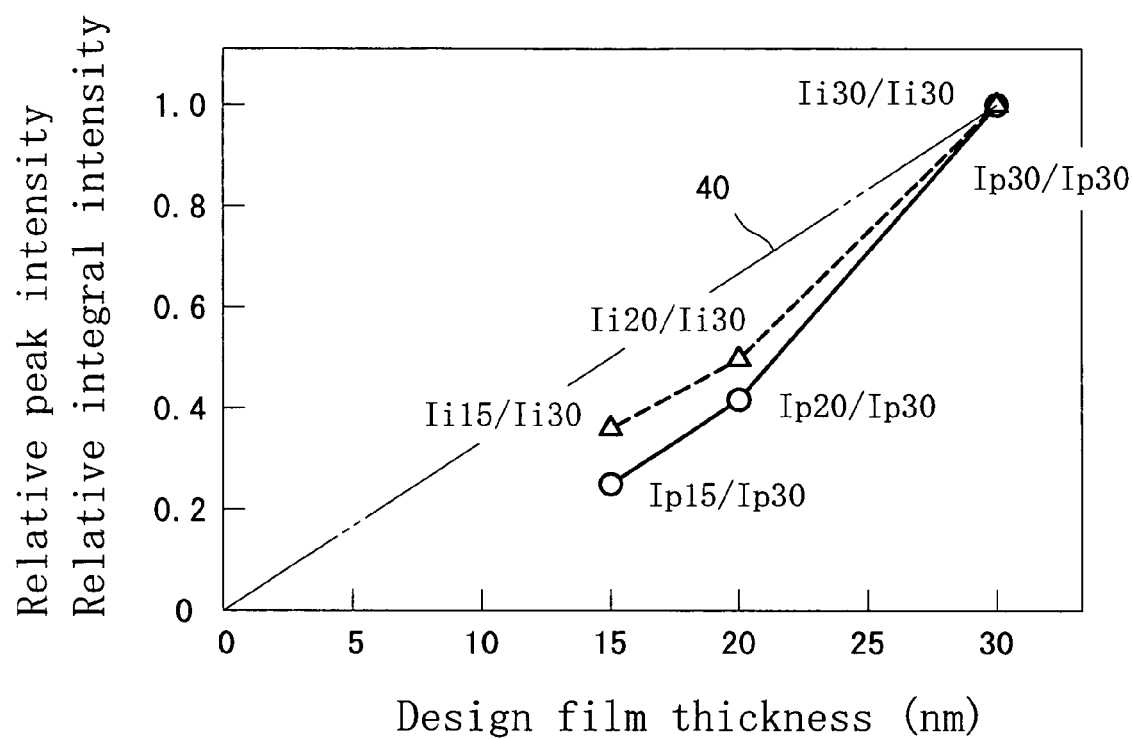
FIG. 2 is a graph indicating relative peak intensities and relative integral intensities of diffracted X-rays from Ta(110) about three kinds of design film thicknesses of tantalum layers.
Figure 14:
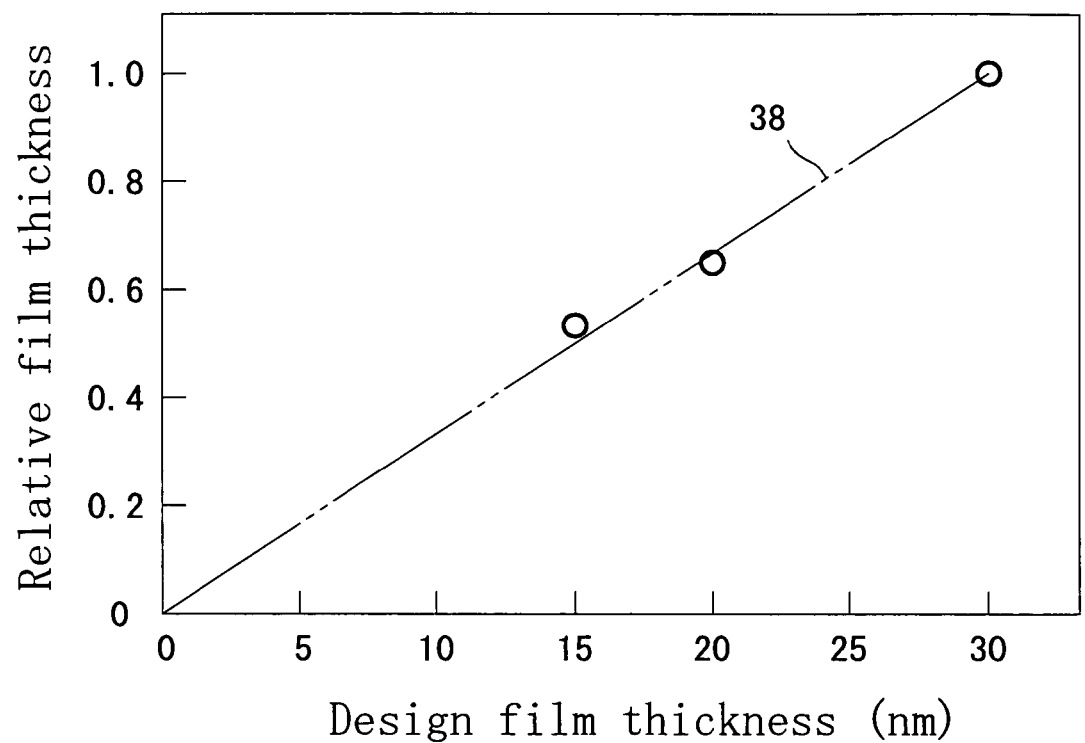
FIG. 14 is a graph showing the measurement results.

FIG. 14 is a graph showing measurement results described above which is comparable to the graph shown in FIG. 2. In the graph shown in FIG. 14, there are plotted the measured film thicknesses of the samples having the design film thicknesses of 20 nm and 15 nm which are divided by the measured film thickness of the standard sample having the design film thickness of 30 nm, that is, the relative film thicknesses. It is seen that the relative film thicknesses for the design film thicknesses of 20 nm and 15 nm exist close to the straight line 38 connecting the origin and the relative film thickness (which is equal to one) of the standard sample having the design film thickness of 30 nm. As will be clearly understood with the comparison between FIG. 14 and FIG. 2, the film thickness measurement method according to the present invention has a higher accuracy than the method based on simply the relative peak intensity or the relative integral intensity.

In the present invention, when the scale factor C can be determined with the use of the standard sample which has the same material as the object thin film and a known film thickness, thereafter a film thickness can be determined in a manner that a rocking curve is measured for the object thin film having an unknown film thickness and the parameter fitting operation can be carried out. Since equation (8) in FIG. 11 takes account of the effect of the X-ray absorption within the thin film, the present invention is applicable to a comparatively large film thickness as long as the X-ray reaches the bottom of the thin film. Accordingly, a comparatively large film thickness which can not be measured based on the X-ray reflectance method can be measured with the present invention. The X-ray reflectance method is applicable to the thickness up to about several hundred nanometers, whereas the film thickness measurement method according to the present invention is applicable to the thickness up to about 1 to 2 micrometers.

Although the standard sample is prepared to be the tantalum thin film having a design film thickness of 30 nm in the embodiment described above, the standard sample may be prepared as described below when the design film thickness is unknown. First, there is prepared a substrate having a density which is far different from the density of tantalum, and only a tantalum layer is deposited on the substrate. The film thickness of the tantalum layer can measured based on the X-ray reflectance method and the resultant measured film thickness can be handled as the known thickness. In this case, since the densities of the tantalum layer and the substrate are far different from each other, the X-ray reflectance method is effective in measuring the film thickness. The thus-prepared tantalum layer is usable as the standard sample in the present invention and the parameter fitting operation of the present invention can be carried out with the standard sample to determine the scale factor C.

The above-described embodiment is characterized by the use of the precisely-determined diffracted X-ray intensity for defining a measured rocking curve. That is, as shown in FIG. 5, the angle 2θ is scanned with the incident angle α being fixed and the integral intensity of the resultant diffraction peak profile is determined so that the determined intensity can be handled as the diffracted X-ray intensity. Further, the thus-determined diffracted X-ray intensities are collected for the respective values of the incident angle α and plotted to obtain a measured rocking curve as shown in FIG. 6. Consequently, the measured rocking curve in FIG. 6 would not be affected by the background and thus equation (8) in FIG. 11 has a form which does not take account of the background.

On the other hand, the present invention is applicable, in principle, to the use of a simplified measured rocking curve in place of the precisely measured rocking curve. Stating in detail, in FIG. 3, the angle of the diffracted X-ray 20 with respect to the incident X-ray 16 is set at and fixed to $2\theta_0$, and only the sample 18 is rotated so that the incident angle α can be changed, and diffracted X-ray intensity is measured to obtain a simplified measured rocking curve. In this case, the measured rocking curve would include the background. If it is desired to use the simplified measured rocking curve, it is necessary to use the theoretical formula which takes account of the background. Assuming that the background part is caused by the scattering object having no preferred orientation, it is contemplated that the variation of the background part with the incident angle α being changed would depend on the irradiated area and on the absorption caused by the thickness of the part which contributes to the background. If the thickness of the part which contributes to the background is considerably small, the variation of the background part with the incident angle α being changed would depend on the irradiated area only. In this case, equation (8) in FIG. 11 can be substituted by equation (10) in FIG. 15, the symbol B in equation (10) indicating the background part.

On the contrary, if the thickness of the part which contributes to the background is large, the variation of the background part with the incident angle α being changed depends on both the irradiated area and the absorption, and then equation (8) in FIG. 11 can be substituted by equation (11) in FIG. 15.

It should be noted that if the good result can not be obtained with the parameter fitting between the simplified measured rocking curve and the theoretical rocking curve based on equation (10) or (11) in FIG. 15, it would be necessary to carry out the parameter fitting between the precisely-determined measured rocking curve as shown in FIG. 6 and the theoretical rocking curve based on equation (8) in FIG. 11.

Although the Gaussian function is selected as the orientation density distribution function in the embodiment described above, other functions may be used. Other functions which are considered to be suitable for the expression of the rocking curve may be the Lorentzian function expressed by equation (12) in FIG. 16, the pseudo-Voight function by equation (13) and the March-Dollase function by equation (14) for instance. The symbol Ga in equation (12) is a normalizing factor for satisfying the normalizing condition of equation (1) in FIG. 8. The symbol G in equation (13) is a normalizing factor expressed by equation (3) in FIG. 8. The symbol Ga in equation (13) is the same as Ga in equation (12). The use of the Gaussian function and the March-Dollase function as the orientation density distribution function is disclosed in the first publication which is cited as the prior art in the Description of the Related Art of this specification.

What is claimed is:

1. A method of measuring a film thickness comprising the steps of:
    (a) preparing a thin film made of a polycrystalline material;
    (b) assuming an orientation density distribution function ρ which is axisymmetric about a normal direction of a surface of said thin film, said orientation density distribution function ρ being a function of an angle φ at which a normal of a measurement lattice plane of a crystallite of the thin film is inclined to a normal of the surface of the thin film, and said orientation density distribution function ρ containing at least one characteristic parameter characterizing a form of the function;
    (c) allowing an X-ray to be incident upon the surface of the thin film at an incident angle α, measuring an intensity of a diffracted X-ray which is reflected at said measurement lattice plane of the thin film, and determining a variation of the intensity of the diffracted X-ray from said measurement lattice plane with the incident angle α being changed to obtain a measured rocking curve;
    (d) calculating a theoretical diffracted X-ray intensity, based on (i) a scale factor which is predetermined for a standard sample having a known film thickness, (ii) said orientation density distribution function ρ and (iii) a film thickness t of said thin film, to obtain a theoretical rocking curve about a variation of the intensity of the diffracted X-ray from said measurement lattice plane with the incident angle α being changed; and
    (e) carrying out a parameter fitting operation in which said characteristic parameter and said film thickness t are adjusted so that said theoretical rocking curve can approach said measured rocking curve as closely as possible, whereby said film thickness t is determined.

2. A method according to claim 1, wherein said orientation density distribution function ρ is a Gaussian function and a full-width-at-half-maximum H of the Gaussian function depends upon a depth z measured from the surface of said thin film.

3. A method according to claim 1, wherein
    said orientation density distribution function ρ is a Gaussian function,
    a full-width-at-half-maximum H of the Gaussian function depends upon a depth z measured from the surface of said thin film,
    said H is equal to a constant value H1 when z is in a range between zero and ηt, where η is in a range between zero and 1,
    said H is equal to another constant value H2 when z is in a range between ηt and t, and
    said parameter fitting operation is carried out with adjusting the three characteristic parameters H1, H2 and η and the film thickness t.

4. A method according to claim 1, wherein said thin film is a tantalum layer deposited on a tantalum nitride layer.

5. An apparatus for measuring a thickness of a thin film made of a polycrystalline material comprising:
    (a) a memory for storing an orientation density distribution function ρ which is axisymmetric about a normal direction of a surface of said thin film, said orientation density distribution function ρ being a function of an angle φ at which a normal of a measurement lattice plane of a crystallite of the thin film is inclined to a normal of the surface of the thin film, and said orientation density distribution function ρ containing at least one characteristic parameter characterizing a form of the function;
    (b) rocking curve measurement means for producing a measured rocking curve in which an X-ray is incident upon the surface of the thin film at an incident angle α, an intensity of a diffracted X-ray which is reflected at said measurement lattice plane of the thin film is measured, and a variation of the intensity of the diffracted X-ray from said measurement lattice plane with the incident angle α being changed is determined;
    (c) theoretical calculation means for producing a theoretical rocking curve about a variation of the intensity of the diffracted X-ray from said measurement lattice plane with the incident angle α being changed in which a theoretical diffracted X-ray intensity is calculated based on (i) a scale factor which is predetermined for a standard sample having a known film thickness, (ii) said orientation density distribution function ρ and (iii) a film thickness t of said thin film; and
    (d) film thickness determination means for determining said film thickness t in which a parameter fitting operation is carried out in a manner that said characteristic parameter and said film thickness t are adjusted so that said theoretical rocking curve can approach said measured rocking curve as closely as possible.

6. An apparatus according to claim 5, wherein said orientation density distribution function $\rho$ is a Gaussian function and a full-width-at-half-maximum H of the Gaussian function depends upon a depth z measured from the surface of said thin film.

7. An apparatus according to claim 5, wherein
said orientation density distribution function $\rho$ is a Gaussian function,
a full-width-at-half-maximum H of the Gaussian function depends upon a depth z measured from the surface of said thin film, said H is equal to a constant value H1 when z is in a range between zero and $\eta t$, where $\eta$ is in a range between zero and 1, said H is equal to another constant value H2 when z is in a range between $\eta t$ and t, and said parameter fitting operation is carried out with adjusting the three characteristic parameters H1, H2 and $\eta$ and the film thickness t.

* * * * *